(12) United States Patent
Clayton et al.

(10) Patent No.: US 10,345,216 B2
(45) Date of Patent: Jul. 9, 2019

(54) SYSTEMS, DEVICES, AND METHODS FOR FLOW CONTROL AND SAMPLE MONITORING CONTROL

(71) Applicant: Research Triangle Institute, Research Triangle Park, NC (US)

(72) Inventors: Anthony Clint Clayton, Rougemont, NC (US); Howard Jerome Walls, Apex, NC (US); David S. Ensor, Chapel Hill, NC (US); Andrei Yurievich Khlystov, Chapel Hill, NC (US)

(73) Assignee: Research Triangle Institute, Research Triangle Park, NC (US)

( * ) Notice: Subject to any disclaimer, the term of this patent is extended or adjusted under 35 U.S.C. 154(b) by 0 days.

(21) Appl. No.: 15/504,727

(22) PCT Filed: Aug. 20, 2015

(86) PCT No.: PCT/US2015/046080
§ 371 (c)(1),
(2) Date: Feb. 17, 2017

(87) PCT Pub. No.: WO2016/028997
PCT Pub. Date: Feb. 25, 2016

(65) Prior Publication Data
US 2017/0268980 A1    Sep. 21, 2017

Related U.S. Application Data

(60) Provisional application No. 62/039,519, filed on Aug. 20, 2014, provisional application No. 62/039,512, filed on Aug. 20, 2014.

(51) Int. Cl.
*G01N 15/00* (2006.01)
*G01N 21/00* (2006.01)
(Continued)

(52) U.S. Cl.
CPC ........... *G01N 15/1404* (2013.01); *C12Q 3/00* (2013.01); *G01N 15/0205* (2013.01);
(Continued)

(58) Field of Classification Search
None
See application file for complete search history.

(56) References Cited

U.S. PATENT DOCUMENTS 3,345,536 A * 10/1967 Atkins ................. B60Q 1/1423
250/214 D
3,520,172 A     7/1970 Liu et al.
(Continued)

FOREIGN PATENT DOCUMENTS

CN       201217660        4/2009
CN       101738628 A      6/2010
(Continued)

OTHER PUBLICATIONS

International Search Report and Written Opinion dated Oct. 23, 2015 from related International Application No. PCT/US2015/046080.
(Continued)

*Primary Examiner* — Shawn Decenzo
*Assistant Examiner* — Jarreas C Underwood
(74) *Attorney, Agent, or Firm* — Olive Law Group, PLLC

(57) ABSTRACT

Sample monitoring and flow control systems and methods are disclosed for monitoring of airborne particulates. A system may include a particle collection filter. The system also includes a fluid moving device for moving a sample through the particle collection filter. Further, the system includes a light source configured to direct irradiating light towards the particle collection filter. The system also includes a light detector positioned to receive the irradiating light passing through the particle collection filter and con-
(Continued)

figured to generate a signal representative of an amount of the received light. Further, the system includes a controller configured to receive the signal and to control the fluid moving device based on the amount of the received light.

12 Claims, 8 Drawing Sheets

(51) Int. Cl.
  G01N 15/14    (2006.01)
  G01N 15/02    (2006.01)
  G01N 15/06    (2006.01)
  G01N 21/53    (2006.01)
  G01N 21/64    (2006.01)
  C12Q 3/00     (2006.01)

(52) U.S. Cl.
  CPC ......... *G01N 15/06* (2013.01); *G01N 15/0625* (2013.01); *G01N 15/1459* (2013.01); *G01N 21/53* (2013.01); *G01N 21/6486* (2013.01); *G01N 2015/0065* (2013.01); *G01N 2015/0693* (2013.01); *G01N 2015/1493* (2013.01); *G01N 2201/062* (2013.01)

(56) References Cited

U.S. PATENT DOCUMENTS

| | | | |
|---|---|---|---|
| 3,770,356 A * | 11/1973 | Kimura | G01N 15/0618 356/38 |
| 3,849,654 A | 11/1974 | Malvin | |
| 4,019,017 A | 4/1977 | Sitek et al. | |
| 4,021,879 A * | 5/1977 | Brigham | A47L 9/2821 15/319 |
| 4,154,669 A | 5/1979 | Goetz | |
| 4,473,296 A | 9/1984 | Shofner et al. | |
| 4,571,079 A | 2/1986 | Knollenberg | |
| 4,879,040 A * | 11/1989 | Prince | A61M 1/34 210/637 |
| 4,917,942 A * | 4/1990 | Winters | A47L 9/14 96/99 |
| 4,921,509 A * | 5/1990 | Maclin | B01D 46/46 55/320 |
| 5,141,309 A * | 8/1992 | Worwag | A47L 9/19 356/72 |
| 5,317,930 A | 6/1994 | Wedding | |
| 5,796,472 A * | 8/1998 | Wirthlin | B01D 46/521 250/227.14 |
| 5,922,976 A | 7/1999 | Russell et al. | |
| 6,263,744 B1 | 7/2001 | Russell et al. | |
| 6,296,425 B1 | 10/2001 | Memory et al. | |
| 6,375,725 B1 * | 4/2002 | Bernard | G01N 21/7703 55/DIG. 34 |
| 6,520,034 B1 | 2/2003 | Masquelier et al. | |
| 6,854,344 B2 | 2/2005 | Cornish et al. | |
| 7,001,451 B2 * | 2/2006 | Kim | B01D 46/0086 356/438 |
| 7,012,685 B1 * | 3/2006 | Wilson | B01D 46/0086 356/239.1 |
| 7,140,265 B2 | 11/2006 | McGill et al. | |
| 8,030,088 B2 | 10/2011 | McCash et al. | |
| 8,531,671 B1 * | 9/2013 | Hansen | G01N 15/0625 356/38 |
| 8,744,780 B2 * | 6/2014 | Wilson, Jr. | G01N 21/59 356/239.1 |
| 8,959,985 B2 * | 2/2015 | Huang | G01N 21/85 73/61.71 |
| 9,109,987 B2 * | 8/2015 | Kinugasa | G01N 15/0211 |
| 9,821,291 B2 * | 11/2017 | Wood | B01J 20/262 |
| 9,915,600 B2 * | 3/2018 | Walls | G01N 15/1436 |
| 2006/0125649 A1 * | 6/2006 | Ostrovsky | G05B 15/02 340/635 |
| 2009/0153857 A1 * | 6/2009 | Matsuda | G01N 15/0205 356/339 |
| 2010/0307119 A1 * | 12/2010 | Leung | B01D 39/1623 55/488 |
| 2011/0049390 A1 | 3/2011 | Murray et al. | |
| 2012/0105839 A1 | 5/2012 | Novosselov et al. | |
| 2013/0008313 A1 * | 1/2013 | Handley | B01D 46/0068 96/11 |
| 2013/0042673 A1 | 2/2013 | Saari-Nordhaus et al. | |
| 2013/0042893 A1 | 2/2013 | Ariessohn et al. | |
| 2014/0017839 A1 | 1/2014 | Li | |

FOREIGN PATENT DOCUMENTS

| | | |
|---|---|---|
| CN | 101762819 A | 6/2010 |
| CN | 101974419 A | 2/2011 |
| CN | 102323111 A | 1/2012 |
| CN | 202393920 U | 8/2012 |
| CN | 102654445 A | 9/2012 |
| CN | 202770678 U | 3/2013 |
| CN | 103115802 A | 5/2013 |
| CN | 103119417 A | 5/2013 |
| CN | 103983544 A | 8/2014 |
| EP | 79079 A1 | 5/1983 |
| ES | 2030992 | 11/1992 |
| GB | 1422188 A | 1/1976 |
| GB | 1538056 A | 1/1979 |
| JP | 10318905 A | 12/1998 |
| JP | 200321219 A | 1/2003 |
| JP | 2004239365 A | 8/2004 |
| JP | 201277784 A | 4/2012 |
| JP | 2012202543 A | 10/2012 |
| KR | 101317982 B1 | 10/2013 |
| SU | 1242768 A1 | 7/1986 |
| SU | 1665267 A1 | 7/1991 |
| WO | 9010858 A1 | 9/1990 |
| WO | 2001095279 A1 | 12/2001 |
| WO | 2005001436 | 4/2005 |
| WO | 2012150958 A1 | 11/2012 |
| WO | 2013123500 A1 | 8/2013 |

OTHER PUBLICATIONS

International Preliminary Report on Patentability from related International Application No. PCT/US2015/046076.
International Preliminary Report on Patentability from related International Application No. PCT/US2015/046080.
International Search Report and Written Opinion dated Oct. 22, 2015 from related application No. PCT/US2015/046080.
Abu-Rahmah, A., et al. (2006). "Integrating nephelometer with a low truncation angle and an extended calibration scheme." Measurement Science & Technology 17(7): 1723-1732.
Agranovski, V., et al. (2003). "Real-time measurement of bacterial aerosols with the UVAPS: performance evaluation." Journal of Aerosol Science 34(3): 301-317.
Ammor, M. S. (2007). "Recent advances in the use of intrinsic fluorescence for bacterial identification and characterization." Journal of Fluorescence 17(5): 455-459.
Greenwood, D. P. et al. (2009). "Optical Techniques for Detecting and Identifying Biological-Warfare Agents." Proceedings of the Ieee 97(6): 971-989.
Hasan, H., et al. (1983). "Integrating nephelometer responses corrections for biomodal size distributions." Aerosol Science and Technology 2(4): 443-453.
Hill, S. C., et al. (2013). "Fluorescence of bioaerosols: mathematical model including primary fluorescing and absorbing molecules in bacteria." Optics Express 21(19): 22285-22313.
Jeys, T. H., et al. (2007). "Advanced trigger development." Lincon Laboratory Journal 17(1): 29-62.
Penaloza, M. A. (199). "Deriving the basic cell-reciprocal integrating nephelometer equation and its use for calibration purposes: a comprehensive approach." Measurement Science and Technology 10(1): R1-R15.
Saari, S., et al. (2014). "Performance of Two Fluorescence-Based Real-Time Bioaerosol Detectors: BioScout vs. UVAPS." Aerosol Science and Technology 48(4): 371-378.

(56) References Cited

OTHER PUBLICATIONS

Sloane, C. S., et al. (1991). "Measurements of aerosol-particle size-improved precision by simultaneous use of optical-particle counter and nephelometer." Aerosol Science and Technology 14(3): 289-301.
Varma, R., et al. (2003). "Toward an ideal integrating nephelometer." Optics Letters 28(12): 1007-1009.
International Preliminary Report on Patentability issued in PCT Application No. PCT/US2015/046076 dated Feb. 21, 2017.
International Preliminary Report on Patentability issued in PCT Application No. PCT/US2015/046080 dated Feb. 21, 2017.
Pahalawatta et al.: "Particle detection and classification in photoelectric smoke detectors using image histogram features.", International Conference on Digital Image Computing: Techniques and Applications (DICTA),pp. 1-8 (2013).
Wallace, Lance: "Real-time measurements of black carbon indoors and outdoors: a comparison of the photoelectric aerosol sensor and the aethalometer, Aerosol", Science and Technology, vol. 39, No. 10, pp. 1015-1025 (2005).
Notice of Allowance issued in counterpart U.S. Appl. No. 15/877,991 dated Mar. 27, 2018.
Extended European Office Action issued in counterpart EP Application No. 15833910 dated Mar. 7, 2018 (eight (8) pages).
Chinese-language Office Action issued in counterpart CN Application No. 201580044164.7 dated Nov. 2, 2018 with English translation (seven (7) pages).
Japanese-language Office Action issued in counterpart JP Application No. 2017-509619 dated Mar. 19, 2019 with English translation (nine (9) pages).

\* cited by examiner

SYSTEMS, DEVICES, AND METHODS FOR FLOW CONTROL AND SAMPLE MONITORING CONTROL

RELATED APPLICATIONS

This application is the national stage of International Application No. PCT/US2015/046080, filed Aug. 20, 2015, titled "SYSTEMS, DEVICES, AND METHODS FOR FLOW CONTROL AND SAMPLE MONITORING CONTROL", which claims the benefit of U.S. Provisional Patent Application Ser. No. 62/039,519, filed Aug. 20, 2014, titled "SYSTEMS, DEVICES, AND METHODS FOR FLOW CONTROL AND SAMPLE MONITORING CONTROL," and U.S. Provisional Patent Application Ser. No. 62/039,512, filed Aug. 20, 2014, titled "DEVICES, SYSTEMS AND METHODS FOR DETECTING PARTICLES," the contents of each of which are incorporated by reference herein in their entireties.

TECHNICAL FIELD

The present invention relates to systems, devices, and methods for flow control and sample monitoring control for the purpose of monitoring airborne particulates.

BACKGROUND

Detection of particles and colloids suspended in a fluid medium for measurement of concentration or other properties is useful in a variety of applications such as medical diagnostics, scientific research, air quality measurements, and threat detection. An example apparatus for determining carbon particle concentration in combustion exhaust is described in U.S. Pat. No. 8,531,671. Another example system for material analysis is described in U.S. Pat. No. 8,411,272. Examples include measurement of the concentration of airborne particles in inside environments such as buildings as well as outside environments.

One application of note is the measurement of the concentration and other properties of airborne particles (or particulate matter, PM) in aerosols. The United States Environmental Protection Agency (US EPA) has set exposure standards for coarse PM (between 10 μm and 2.5 μm, $PM_{10}$) and fine PM (less than 2.5 μm, $PM_{2.5}$) due to the importance of aerosol concentration in the air and its health effects. Aerosol concentrations are also important in the manufacturing industry for both protection of the health of workers and preventing contamination in the manufacturing process.

A class of aerosols of special interest is bioaerosols. Bioaerosols include bio-particles such as fungus spores, bacteria spores, bacteria, viruses, and biologically derived particles (skin cells, detritus, etc.). Some bioaerosols cause chronic and/or acute health effects, for example certain strains of black mold or *Bacillus anthraces* (causative bacteria of anthrax). Bioaerosol concentrations are important in maintaining safe hospitals, clean food processing, pharmaceutical and medical device manufacturing, and air quality. Airborne spread of diseases is of particular concern from a public health perspective. Aerosolized bioagents can also be used by terrorists to harm civilian or military populations.

Measurement (sensing) of aerosol and bioaerosol concentration is typically accomplished with optical techniques. Aerosol (e.g., solid and liquid particles ≤10 μm dispersed in air) concentration measurement is readily achieved by various light scattering measurements. The most accurate method entails the use of a single particle counter that focuses a stream of aerosol into a detection cavity where light scattering from a long wavelength (>650 nm) laser is measured. Precision optics are required to collect and focus the scattered light (while excluding the source light) onto a photon detector. The photon detectors are made from silicon or photocathode materials (e.g., indium gallium arsenide) that undergo the photoelectric effect (convert photons to electrons). These materials are packaged into detectors that offer high amplification of the signal from the photons, such as photomultiplier tubes (PMTs) and avalanche photodiodes (APDs). These detectors have active detection areas that are small (less than 25 $mm^2$) and limited to planar geometries. Moreover, these detectors cost $100 or more, often exceeding $1,000 in the case of a high sensitivity PMT.

Autofluorescence (or intrinsic fluorescence) excited by ultraviolet (UV) and blue light is well-developed for detection of bioaerosols. See Hairston et al., "Design of an instrument for real-time detection of bioaerosols using simultaneous measurement of particle aerodynamic size and intrinsic fluorescence," *Journal of Aerosol Science* 28(3): 471-482 (1997); Ho, "Future of biological aerosol detection," *Analytical Chimica Acta* 457(1): 125-148 (2002); Agranovski et al., "Real-time measurement of bacterial aerosols with the UVAPS: Performance evaluation," *Journal of Aerosol Science* 34(3): 301-317 (2003); Ammor, "Recent advances in the use of intrinsic fluorescence for bacterial identification and characterization," *Journal of Fluorescence* 17(5): 455-459 (2007); Ho et al., "Feasability of using real-time optical methods for detecting the presence of viable bacteria aerosols at low concentrations in clean room environments," *Aerobiologia* 27(2): 163-172 (2011). Exploiting autofluorescence of microbes is widely viewed as one of the most cost-effective means to detect a potential biological threat. Bioaerosol detectors typically use a combination of light scattering (measurement of general aerosol concentration and properties) and autofluorescence (detection of emitted photons). Bioaerosol detectors based on autofluorescence rely on fluorescence from molecular fluorophores that reside within the bio-particle. For clean bio-particles, this fluorescence can be primarily attributed to biochemicals such as tryptophan and tyrosine (amino acids), nicotinamide adenine dinucleotide (NADH), and riboflavin. NADH and riboflavin absorb and emit longer wavelengths than the amino acids. See Jeys et al., "Advanced trigger development," *Lincoln Laboratory Journal* 17(1): 29-62 (2007); Hill et al., "Fluorescence of bioaerosols: mathematical model including primary fluorescing and absorbing molecules in bacteria," *Optics Express* 21(19): 22285-22313 (2013). The ability to use longer wavelength excitation sources such as light-emitting diodes (LEDs, excitation wavelength $\lambda_{exc}$>360 nm) or lasers ($\lambda_{exc}$>400 nm) may reduce the cost of such instruments.

Traditional bioaerosol particle detectors rely on three main components: (1) an excitation source of appropriate wavelength to excite a targeted fluorophore or collection of fluorophores; (2) precision optics (lenses and minors) on both the excitation and emission side to focus the source onto the narrow air stream and to enhance the collection of emitted photons from biological particles; and (3) a high gain detector such as a PMT or APD. Elastic light scattering from visible or long wavelengths is utilized to count and sometimes size the particles. Autofluorescence of biomolecules is utilized to detect microorganisms. The typical bioaerosol detector utilizes a small detection cavity, with fluorescence active volumes on the order of $1\times10^{-4}$ $cm^3$, making the window for detection of each bioaerosol particle exceedingly small. At typical flow rates, a bioaerosol particle resides within the excitation volume for 1-10 µs on average. See Hairston et al. (1997). As a result, emitted and scattered light from each bioaerosol particle is collected virtually on an individual basis, and the signal is weak. See Greenwood et al., "Optical Techniques for Detecting and Identifying Biological Warfare Agents," *Proceedings of the IEEE* 97(6): 971-989 (2009). This weak signal thus requires the use of precision lenses and mirrors to collect the weak signal and focus it onto the high gain detector (e.g., PMT or APD).

Measurement of aerosol and bioaerosol concentration and changes in concentration is possible via a variety of commercially available instruments such as the Laser Aerosol Spectrometer for aerosols (TSI Incorporated, Shoreview, Minn., USA), the Ultraviolet Aerodynamic Particle Sizer for bioaerosols (TSI Incorporated), the Wideband Integrated Bioaerosol Sensor (WIBS-4) for bioaerosols (Droplet Measurement Technologies, Boulder, Colo., USA), and the instantaneous biological analyzer and collector (FLIR Systems, Inc., Wilsonville, Oreg., USA). However, such instruments can exceed $10,000 in cost making wide spread use cost prohibitive. Furthermore, having a sufficiently dense sensor network of aerosol/bioaerosol sensors (i.e., multiples of these instruments in communication with a central network) is cost prohibitive. The high cost of a sensor network also means that capitalizing on responsive systems is challenging. For example, it would be desirable to provide several bioaerosol sensors positioned throughout a hospital or other building and networked with the building's control systems to maintain a safe environment and respond to a change in bioaerosol concentration, such as by diverting airflow or indicating the need for maintenance of filters and air handlers.

Aerosol exposure monitors have been developed that acquire data from aerosol while the aerosol is sampled in real time during a prescribed sampling period (integration period). Such devices may employ inertial impactors for aerodynamic sizing, particle collection filters for collection and subsequent analysis, and nephelometers for measuring particle concentration by acquiring light scattering data in real time. Examples of such devices are described in International Publication No. WO 2013/063426, filed Oct. 26, 2012, titled "AEROSOL EXPOSURE MONITORING," the content of which is incorporated by reference herein in its entirety. Also known are turbidometers, which measure the concentrations of particles such as cells in solution.

In collecting air samples for the purpose of air quality monitoring, maintaining a constant flow rate is important. However, as a filter loads with particles, the pressure drop increases and results in reduced flow. This changing of the flow rate with time can lead to inaccurate quantification of the amount of aerosol or other sample present. Accordingly, there is a need for systems and techniques for managing flow rate.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to embodiments, a sample monitoring control system includes a particle collection filter. The system also includes a fluid moving device for moving a sample through the particle collection filter. Further, the system includes a light source configured to direct irradiating light towards the particle collection filter. The system also includes a light detector positioned to receive the irradiating light passing through the particle collection filter and configured to generate a signal representative of an amount of the received light. Further, the system includes a controller configured to receive the signal and to control the fluid moving device based on the amount of the received light.

In accordance with embodiments, a method for sample monitoring control includes using a fluid moving device to move a sample through a particle collection filter. The method also includes directing irradiating light towards the particle collection filter. Further, the method includes determining an amount of the irradiating light passing through the particle collection filter. The method also includes controlling the fluid moving device based on the amount of the received light.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION

As used herein, the term "aerosol" generally refers to an assembly of liquid or solid particles (or particulates, or particulate matter) suspended in a gaseous medium long enough to be observed and measured. The size of aerosol particles typically ranges from about 0.001 µm to about 100 µm. See Kulkarni et al., Aerosol Measurement, $3^{rd}$ ed., John Wiley & Sons, Inc. (2011), p. 821. The term "gaseous fluid" generally refers to a gas (or gaseous fluid, or gas-phase fluid). A gas may or may not contain liquid droplets or vapor, and may or may not contain aerosol particles. An example of a gas is, but is not limited to, ambient air. An aerosol may thus be considered as comprising particles and a gas that entrains or carries the particles.

As used herein, the term "bioaerosol" generally refers to an aerosol in which one or more bio-particles are suspended or carried. The term "bio-particle" generally refers to a biological material, or the combination of a biological material and a non-biological particle on which the biological material is carried. That is, a biological material may itself be a particle freely suspended in an aerosol, or may be carried on a non-biological particle such that the biological material and the non-biological particle are suspended together in the aerosol. The biological material may be carried on the non-biological particle by any mechanism such as, for example, entrapment, embedment, adhesion, adsorption, attractive force, affinity, etc. Examples of biological materials include, but are not limited to, spores (e.g., fungal spores, bacterial spores, etc.), fungi, molds, bacteria, viruses, biological cells or intracellular components, biologically derived particles (e.g., skin cells, detritus, etc.), etc.

As used herein, for convenience the term "aerosol" generally encompasses the term "bioaerosol" and the term "particle" generally encompasses the term "bio-particle," unless indicated otherwise or the context dictates otherwise.

As used herein, the term "fluid" generally encompasses the term "liquid" as well as term "gas" (e.g., aerosol), unless indicated otherwise or the context dictates otherwise. Particles suspended or carried in a liquid, as well as particles suspended or carried in an aerosol, may be detected by devices and methods disclosed herein.

As used herein, the term "sample" may encompass the terms aerosol, bioaerosol, gas, or fluid.

As used herein, the term "light" generally refers to electromagnetic radiation, quantizable as photons. As it pertains to the present disclosure, light may propagate at wavelengths ranging from ultraviolet (UV) to infrared (IR). In the present disclosure, the terms "light," "photons," and "radiation" are used interchangeably.

As used herein, a material is "optically transparent" if it is able to efficiently pass (with minimal optical transmission loss) light of a desired wavelength or range of wavelengths.

Figure 1:
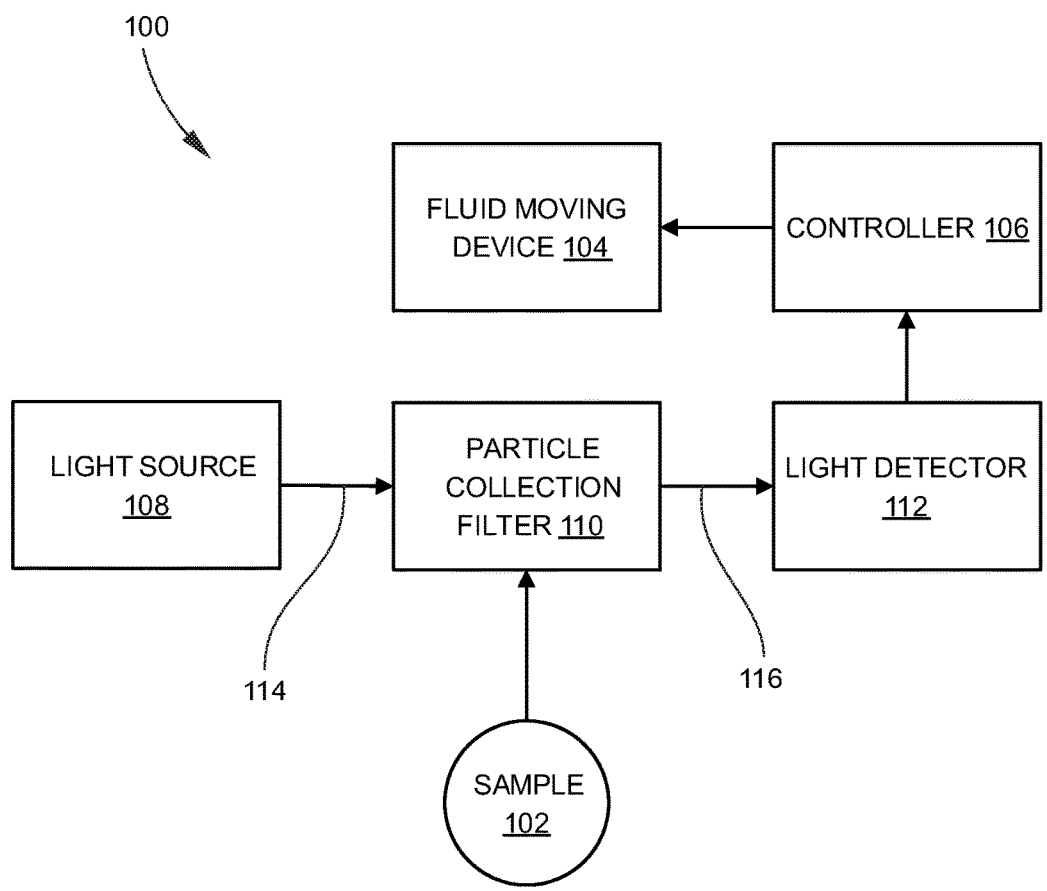
FIG. 1 is a block diagram of an example sample monitoring control system in accordance with embodiments of the present disclosure.

FIG. 1 is a block diagram of an example sample monitoring control system 100 in accordance with embodiments of the present disclosure. The sample monitoring control system 100 may be part of a particle detector that defines a sample chamber or detection cavity through which a particle-laden sample (i.e., aerosol or liquid) 102 may flow. Referring to FIG. 1, the system 100 includes a fluid moving device 104 configured to move the sample 102 through the sample chamber. The fluid moving device 104 may be a fan. A controller 106 may be communicatively connected to the fluid moving device 104 for controlling output of the fluid moving device 104. The controller 106 may be configured to control the fluid moving device 104 such that the sample 102 is moved through the sample chamber at a constant rate, near constant rate, or other desired rate.

The system 100 includes a light source 108, a particle collection filter 110, and a light detector 112. The light source 108 may be configured to generate and to direct one or more beams of irradiating light 114 towards the particle collection filter 110. The irradiating light 114 may be one or more selected wavelengths. In an example, the light source 108 includes one or more light emitting diodes (LEDs) configured to generate light of one or more wavelengths. As an example, the irradiating light 114 may be in a wavelength range effective for inducing autofluorescence in one or more types of bioparticles collected on the filter 110. Emitted fluorescence light 116 may be used to identify and quantify spores, bacteria, and/or other particulates. The light detector 112 and/or one or more other light detectors may be suitably positioned within the sample chamber for receiving the fluorescence light 116 and for generating a representative electrical signal. In another example, the light 116 may be transmitted light or scattering light from the collected particles that is measured by the light detector 112.

A data acquisition device may be communicatively connected to the light detector 112 for receiving the output signal. The data acquisition device may be configured to analyze the signal and to present indication of detected particulates to an operator. For example, the data acquisition device may be configured to measure a response of photo-responsive (e.g., photovoltaic, photoelectric, etc.) material. The response may include, but is not limited to, a voltage response, a current response, a resistance response, or a combination of two or more of the foregoing. The data acquisition device may be a computing device (e.g., computer) configured to receive the output signal and including one or more processors and memory having instructions for implementing analysis and presentation functions. The system 100 may include one or more other light detectors having a photo-responsive material configured for receiving measurement light from the sample.

In some embodiments, the system 100 includes a filter holder such as a housing that supports the particle collection filter 110 and also defines a sample chamber with a sample inlet on the upstream side of the particle collection filter 110 and a sample outlet on the downstream side of the particle collection filter 110. The fluid moving device 104 may be positioned either inside of or external to the filter holder or housing to establish a flow of sample-containing fluid through the filter holder or housing. The light source 108 and the light detector 112 may also be positioned either inside of or external to the filter holder or housing as needed to establish, respectively, a path or paths for irradiating light 114 from the light detector 112 to the particle collection filter 110, and a path or paths for measurement (e.g., transmitted, scattered, or fluorescence) light 116 from the particle collection filter 110 to the light detector 112.

In some embodiments, the particle collection filter 110 is periodically replaced and may be either shipped to a central lab for analysis or analyzed on-site utilizing an off-line optical detection system, which may be an LED-based system and is preferably a low-cost system. As one example, the off-line optical detection system may be based on an integrated sphere design. Multiple LEDs with different emission wavelengths may be utilized to derive light scattering aerosol properties. The detection system may also be configured to obtain information on the basic chemical make-up of the particles (e.g., sulfate, organic and black carbon, etc.). In other embodiments, the filter holder or housing may be configured such that it serves as an integrated sphere or light transmission/scattering device with the light detector 112 incorporated into its body. In this configuration the particle detector/sampler aspect of the system 100 may be operated semi-autonomously, requiring infrequent changes of the particle collection filter 110, which may then be sent to a central lab for analysis, random quality control checks, or other detailed analysis. Such an on-line detection system may also be adapted for measurements of bio-aerosols by using UV LEDs of one or more wavelengths to excite fluorescence of biological molecules in the collected aerosol particles. The emitted fluorescent light may then be utilized to identify and quantify spores, bacteria and other biological particulates. In other embodiments, to increase sensitivity of the device, the integrated sphere may be replaced with a light collection device that uses a flexible solar panel instead of a photoresistor, as described further below. By utilizing a larger collection area, more light is harvested, improving the sensitivity of the device.

The particle collection filter 110 may be a nanofiber filter. The particle collection filter 110 may include multiple fibers. In an example, the fibers may be formed into a fiber mat and configured to collect particles (e.g., particles from pollution or biological molecules) thereon. The fibers may, for example, have an average fiber diameter of less than 500 microns. Examples for preparing the nanofiber filter material are provided in U.S. Pat. Nos. 8,652,229 and 7,789,930, the disclosures of which are incorporated herein by reference. Other examples for preparing the nanofiber filter material are provided in PCT International Patent Application No. PCT/US2013/073620 (Publication No. WO2014089458), the disclosure of which is incorporated herein by reference. Alternatively, any other suitable techniques may be used for fabricating nonwoven filter media from filter media from nanofibers. For example, techniques may include, but are not limited to, Forcespinning (FibeRio), XanoShear (liquid shearing; Xanofi), and advanced melt blowing.

For example, a solution containing 21 wt % polysulfone (Udel P3500 LCD by Solvay Advanced Polymers) in dimethylacetamide with 0.2 wt. % tetrabutylammonium chloride may be flowed through a 30 gauge stainless steel needle with a flow rate of approximately 0.05 ml/hr. A potential of 29.5 kV DC can be applied to the needle with a grounded substrate located 25.4 cm away from the needle. A mixture of dry and wetted (via bubbling through deionized water) carbon dioxide can be used to obtain an RH in the range of 26 to 38% as described by U.S. Pat. Nos. 7,297,305 and 7,762,801, the disclosures of which are incorporated herein by reference. The nanofibers are deposited via electrospinning onto an appropriate support (substrate) such as a lightweight nonwoven material such as Reemay 2250 or Reemay 2016 (PGI/Fiberweb).

The Reemay substrates can be spunbound polyester nonwovens with negligible collection efficiency for 0.3 micron aerosols and high air flow permeability. Textest air permeability of 2250 is 6641 liters per square meter per second (L/m$^2$/s) and for 2016 is 2785 L/m$^2$/s. The materials may be light weight; basis weight of 2250 is 17.0 g/m$^2$ and for 2016 is 45.9 g/m$^2$. The translucency (light transmittance) of the substrate is important. The transmittance at 520 nm should be greater than 50%. Various substrates are acceptable as substrates for the nanofibers and are not restricted to spunbound polyester nonwovens. Materials can include, but are not limited to, nylon, polypropylene, polyurethanes, polycarbonate, polyimide, polyamide, and other synthetic polymers in nonwoven or woven formats. Metal meshes or screens may also be acceptable such as woven stainless steel or aluminum similar to that used in window screen. The important features are that the air permeability is high (greater than 800 L/m$^2$/s) and fairly translucent (transmittance at 520 nm more than 40%). The purpose of the support is merely to provide structural strength to the nanofibers. In some embodiments, free-standing nanofiber filter material with sufficient strength may be utilized.

In addition to polysulfone for making nanofibers, other example polymers include, but are not limited to, acrylonitrile/butadiene copolymer, cellulose, cellulose acetate, chitosan, collagen, nylon, poly(acrylic acid), poly(chloro styrene), poly(dimethyl siloxane), poly(ether imide), poly(ether sulfone), poly(ethyl acrylate), poly(ethyl vinyl acetate), poly (ethyl-co-vinyl acetate), poly(ethylene oxide), poly(ethylene terephthalate), poly(lactic acid-co-glycolic acid), poly (methacrylic acid) salt, poly(methyl methacrylate), poly (methyl styrene), poly(styrene sulfonic acid) salt, poly(styrene sulfonyl fluoride), poly(styrene-co-acrylonitrile), poly (styrene-co-butadiene), poly(styrene-co-divinyl benzene), poly(vinyl acetate), poly(vinyl alcohol), poly(vinyl chloride), poly(vinylidene fluoride), polyacrylamide, polyacrylonitrile, polyamide, polyaniline, polybenzimidazole, polycaprolactone, polycarbonate, poly(dimethylsiloxane-co-polyethyleneoxide), poly(etheretherketone), polyethylene, polyethyleneimine, polyimide, polyisoprene, polylactide, polypropylene, polystyrene, polysulfone, polyurethane, poly (vinylpyrrolidone), poly(2-hydroxy ethyl methacrylate) (PHEMA), gelatin, proteins, SEBS copolymer, silk (natural or synthetically derived), and styrene/isoprene copolymer.

Ideally the final structure of nanofiber filter material with substrate (or in some embodiments a "free-standing" nanofiber filter material) should have an aerosol filtration efficiency of better than 90%, be fairly translucent (transmittance of 520 nm light of at least 50%), and have a pressure drop of less than 125 Pa for a face velocity of 5.3 cm/s. The thickness of the filter media, the diameter of the fibers, and the three-dimensional arrangement of the fibers (orientation, packing density, uniformity of dispersion) determine the filtration and pressure drop properties. These structural features and the polymer chemistry determine the optical properties. The impact of nanofiber structure on optical properties and tuning optical properties is discussed in U.S. Patent Application Publication No. 2010/0177518, the content of which is incorporated by reference herein Filter materials other than nanofibers are also possible along with some compromise in the performance of the filter material. Example filter materials include, but are not limited to, expanded polytetrafluoroethylene (ePTFE; better known as expanded Teflon), polycarbonate membrane filters, microfiber glass, and other filter materials used in air sampling. The filter material may be configured to exhibit a filtration efficiency of at least 85%, a transmittance at 520 nm of at least 30%, and a pressure drop not more than 600 Pa for a face velocity of 5.3 cm/s. One such filter is the Teflo filter made by Pall.

Figure 8:
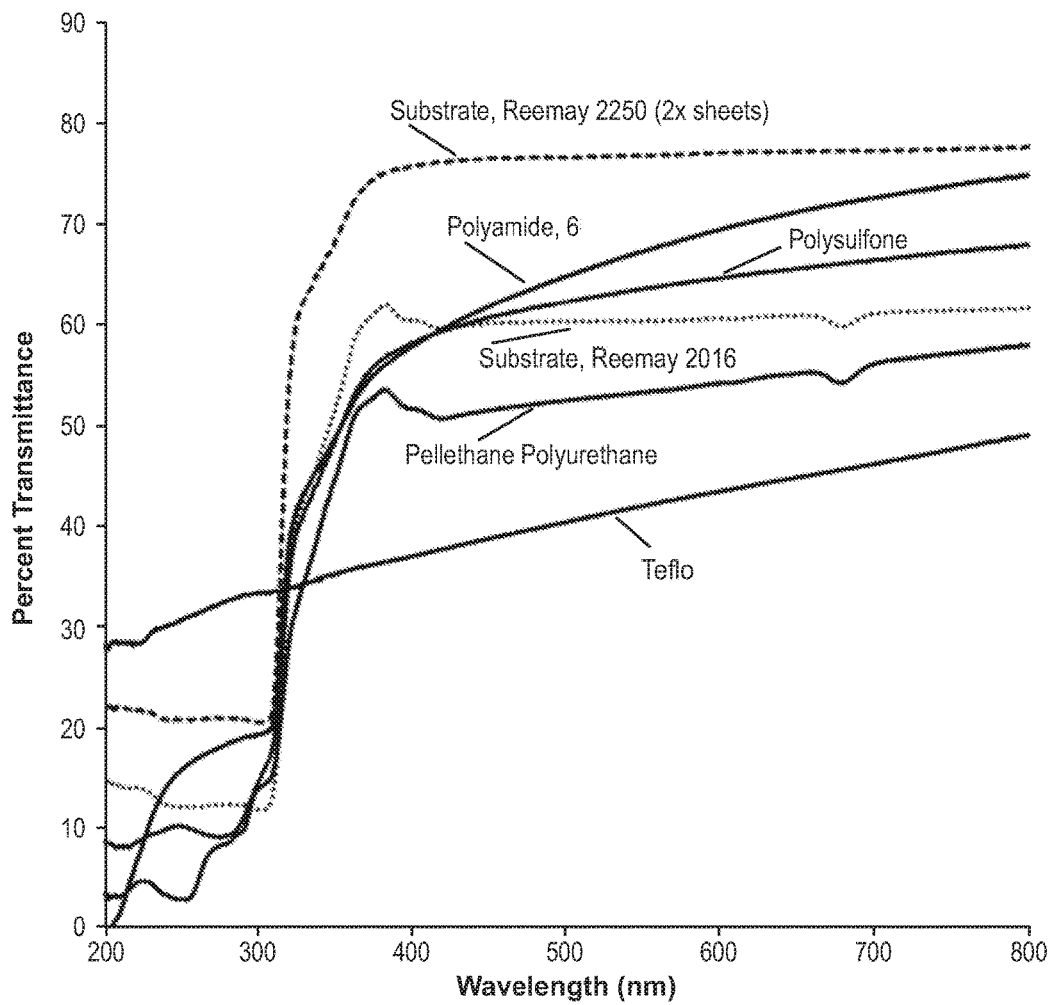
FIG. 8 is a plot of percent transmittance as a function of light wavelength for various filter materials and the Reemay substrates used with some of the nanofiber filter materials.

The table below summarizes the typical performance values for various filter materials. FIG. 8 is a plot of percent transmittance as a function of light wavelength for various filter materials and the Reemay substrates used with some of the nanofiber filter materials. Note than in some applications it may be desired that the % transmittance curve be fairly flat over the wavelengths of interest (e.g. 400 nm to 620 nm). However, the background adsorption of the filter material can be subtracted (calibrated out).

| Material | Eff (%) | ΔP (Pa) | % T@520 nm |
|---|---|---|---|
| Nanofiber Polyamide 6 | 94.5% | 110 | 62.3% |
| Nanofiber Polysulfone | 91.7% | 37 | 67.7% |
| Nanofiber Pellethane* | 90.4% | 49 | 52.4% |
| Teflo | 99.998% | 487 | 40.9% |

*Pellethane polyurethane by Lubrizol

As mentioned, the fluid moving device 104 may be controlled such that the sample 102 is moved through the sample chamber at a constant rate or near constant rate. Particularly, the light detector 112 may be positioned to receive at least a portion of the light 116 passing through the particle collection filter 110. For example, the light source 108 and the light detector 112 may be positioned within the sample chamber and on opposing sides of the particle collection filter 110. The light detector 112 may include one or more photo resistors or photo cells.

The controller 106 may be communicatively connected to the light detector 112 for receiving a signal representative of light received by the light detector 112. For example, the signal may be representative of an amount of light received by the light detector 112 that passed through the particle collection filter 110. The controller 106 may be configured to control the fluid moving device 104 to increase and/or decrease a fluid moving output of the fluid moving device 104 based on the amount of the received light. For example, the controller 106 may control the fluid moving device 104 to increase an output of the fluid moving device 104 in response to a decrease in the amount of the received light. In another example, the controller 106 may control the fluid moving device 104 to decrease an output of the fluid moving device 104 in response to an increase in the amount of the received light. The output of the fluid moving device 104 may be controlled such that a flow of the sample 102 is maintained at a constant rate or near constant rate. As particulates collect in the filter 110, increased output of the fluid moving device 104 may be needed to maintain the same flow rate.

The controller 106 may include any suitable hardware, software, firmware, or combinations thereof for controlling output of the fluid moving device 104 based on the amount of received light. For example, the controller 106 may include a micro controller, resistors, voltage regulator(s), the like, and combinations thereof.

Figure 2:
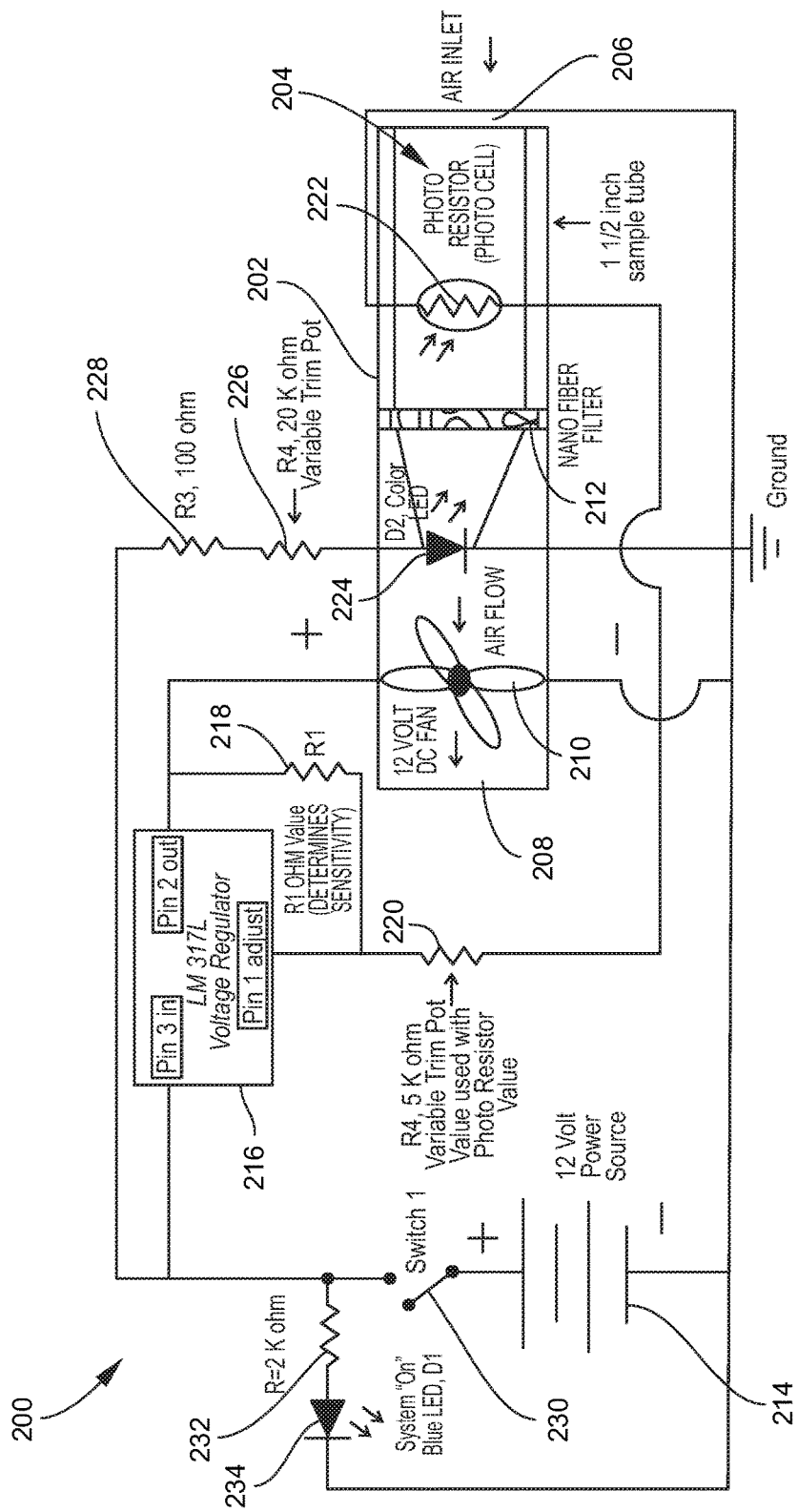
FIG. 2 is a schematic diagram of another example sample monitoring control system in accordance with embodiments of the present disclosure.

FIG. 2 illustrates a schematic diagram of another example sample monitoring control system 200 in accordance with embodiments of the present disclosure. Referring to FIG. 2, the system 200 includes a housing 202 defining and enclosing a sample chamber, generally designated 204, within an interior space. Further, the housing 202 defines a sample inlet 206 and a sample outlet 208. The housing 202 may be a 1.5 inch sample tube. Alternatively, for example, the housing 202 may be any other suitable size and shape.

The system 200 may include a fan 210 or other fluid moving device for drawing a sample into the sample chamber 204 via the sample inlet 206. The fan 210 may also move the sample from the sample chamber 204 and outside via the sample outlet 208. Sample passing through the sample chamber 204 may move through a particle collection filter 212. The particle collection filter 212 may be sized and positioned within the sample chamber 204 to intercept at least a portion of sample flowing through the sample chamber 204.

A power source 214 may supply power to the fan 210. The power source 214 may be a 12 volt DC supply source (e.g., battery or otherwise) connected to the fan 210 for supplying voltage to the fan 210. More particularly, for example, the power source 214 may supply voltage to an adjustable voltage regulator 216 (e.g., an LM317 voltage regulator made available by National Semiconductors). The DC voltage output of the voltage regulator 216 can in turn control the amount of voltage supplied to the fan 210. A lower voltage applied to the fan 210 results in a lower inlet air flow because the output of the fan 210 is reduced. Conversely, a higher voltage applied to the fan 210 results in a higher inlet air flow because the output of the fan 210 is increased.

In this example, the voltage output of the voltage regulator 216 is controlled by the resistance value seen in the circuit by resistor R1 218 and the total resistance seen by resistor R2 220. The value of resistor R1 218 determines the range of the circuit in terms of raising or lowering the voltage threshold, which may be considered the "sensitivity." For example, an R1 value of 500 ohms and an R2 value of 2300 ohms can produce an output voltage of 7 volts DC. By increasing the R1 value to 600 ohms, but keeping the R2 value the same at 2300 ohms, a lower voltage output of 6 volts DC is supplied to the fan 210. Another example involves lowering the R1 value to 400 ohms and keeping the R2 value at 2300 ohms to produce an output of 8.4 volts DC. The equation for the output of the voltage regulator 216 may be represented by the following equation:

$$V_{out} = 1.25 * \left(1 + \frac{R2}{R1}\right).$$

The variable 5 Kohm resistor R2 220 is connected in series with a photo resistor 222 (or any other suitable light detector). The photo resistor 222 is mounted or otherwise positioned to face in toward an inlet side (upstream side) of the filter 212. An LED (or other suitable light source) 224 may be center positioned within the sample chamber 204. The LED 224 is positioned away from and on the downstream side (back side) of the filter 212. The brightness level of the LED 224 may be suitably set by a variable resistor R4 (or potentiometer) 226. A resistor R3 228 may be placed in series with the resistor R4 226 (e.g., a 100 ohm resistor). In an example, the variable resistor R4 226 is a 20 Kohm variable resistor. The resistance value of the photo resistor 222 decreases with exposure to light from a value of a few hundred ohms with light, to a value of several Kohms when it detects less light.

When the filter 212 begins to load with material (e.g., particulates), the transmittance of the LED light passing through the filter 212 is decreased. The reduced light seen by the photo resistor 222 causes the total R2 resistance value to increase, which causes the circuit to see more resistance and increase the voltage output of the voltage regulator 216 to the fan 210. As a result, the output of the fan 210 is controlled to increase, and thus the flow rate increases in response. Depending on the concentration and makeup of the sample being monitored, this response may take a variable amount of time (e.g., days, minutes, or hours). The output of the fan 210 may continue to increase with filter loading until a maximum output voltage of the voltage regulator 216 is reached. This output voltage may depend on the total supply voltage and may be increased to handle denser filters given the parameters of the fan being used.

It is noted that in the example of FIG. 2, various components are described as controlling fluid moving through the sample chamber 204 based on the amount of light received at the photo resistor 222. These components may be considered all part of a controller for the fan 210. Although specific components and functions are described for implementing this function, it should be understood that any suitable hardware, software, firmware, or combinations thereof may be utilized for implementing this function. For example, a micro controller may be utilized.

The power source 214 may be connected to a switch 230 for turning on and off the system 200. In addition, the system 200 may include a resistor 232 and a LED 234 connected in parallel with the switch 230 and power source 214 for use in indicating whether the system 200 is turned on or off.

Figure 3:
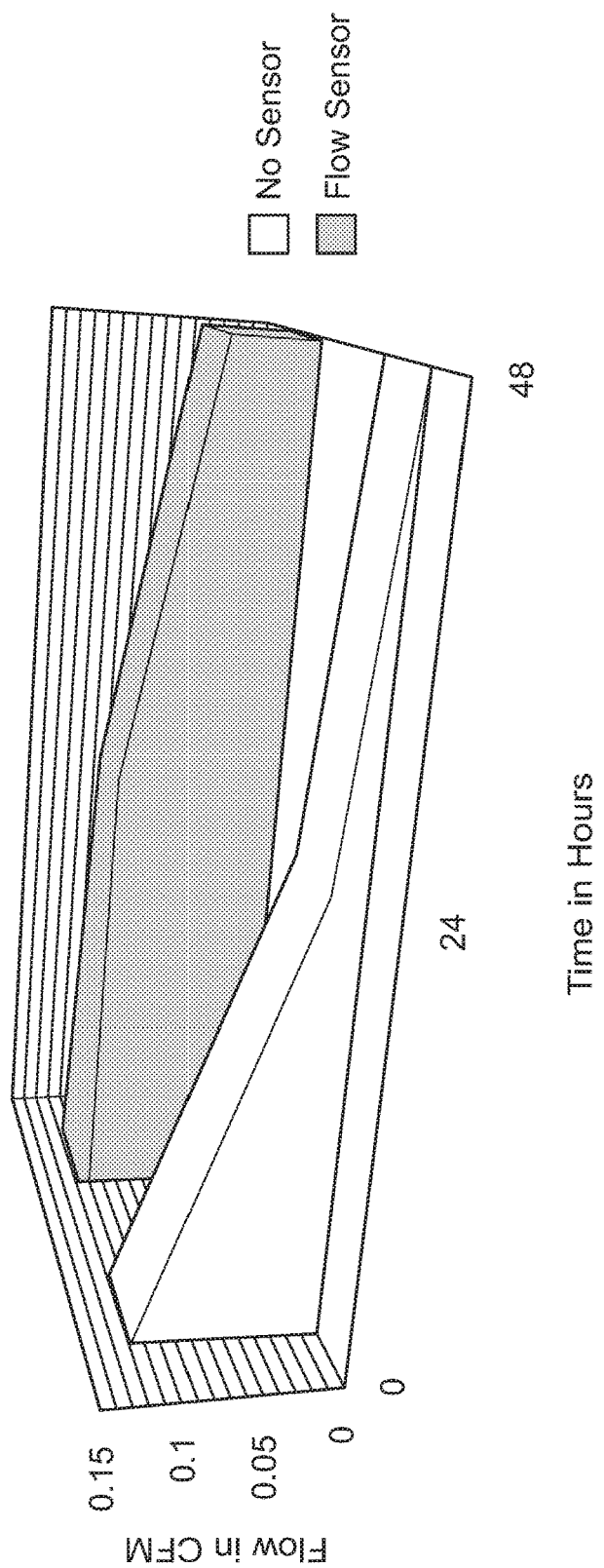
FIG. 3 is a graph showing sampling flow rate during filter loading with and without a controller or flow control circuit as shown in FIG. 2.

FIG. 3 illustrates a graph showing sampling flow rate during filter loading with and without a controller or flow control circuit as shown in FIG. 2. Particularly, FIG. 3 shows the effect of voltage control on flow stability. If the fan 210 is operated without flow control, the accumulation of particulates on the filter 212 increases resistance to flow, causing the flow rate to reduce and decreasing the filter loading over time. The graph shows that the controller significantly improves flow stability, increasing accuracy of sampling.

In experiments, the system was placed in a lab freezer for many hours. This experiment demonstrated that the system operates normally even at −24° C. During the experiment, the system was placed in a freezer and monitored every hour to check for continued fan operation.

Figure 4:
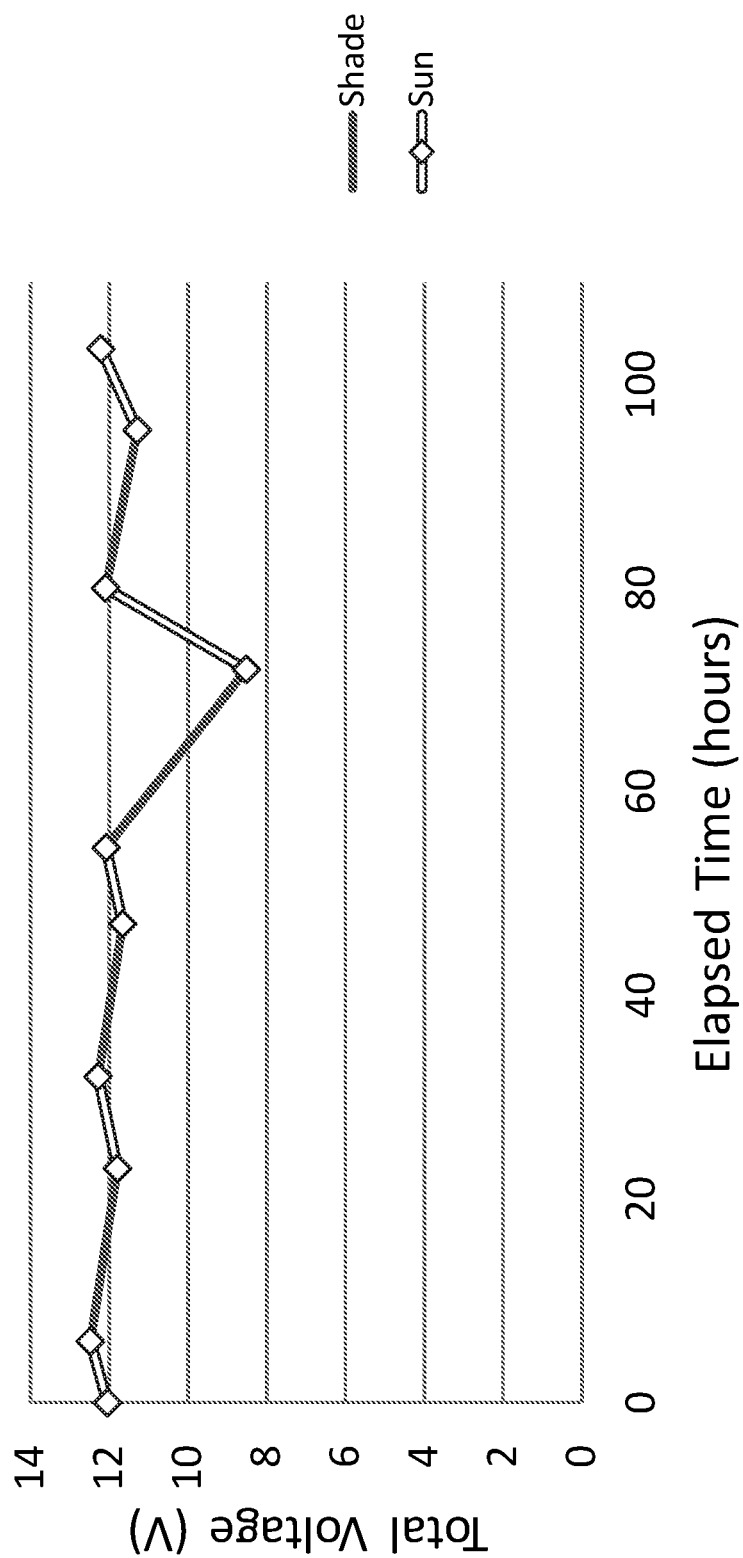
FIG. 4 is a graph of supply output with the solar panel in accordance with embodiments of the present disclosure.

In an example, a set of AA batteries may be used as a power source for the system. Such batteries can last between 12 and 24 hours, depending on the sample loading (higher loadings reduce durability, as more power is required to maintain the sampling flow). For extended use, a solar panel may be used to operate the system and recharge the batteries. In experimental conditions that changed from sunny to cloudy, the system operated with a solar panel for 57 hours on one test, and 103 hours on another test. This solar panel supply voltage test is shown in FIG. 4, which illustrates a graph of supply output with the solar panel. The plot in FIG. 4 shows the supply voltage during sun and shade while being run continuously.

Figure 5:
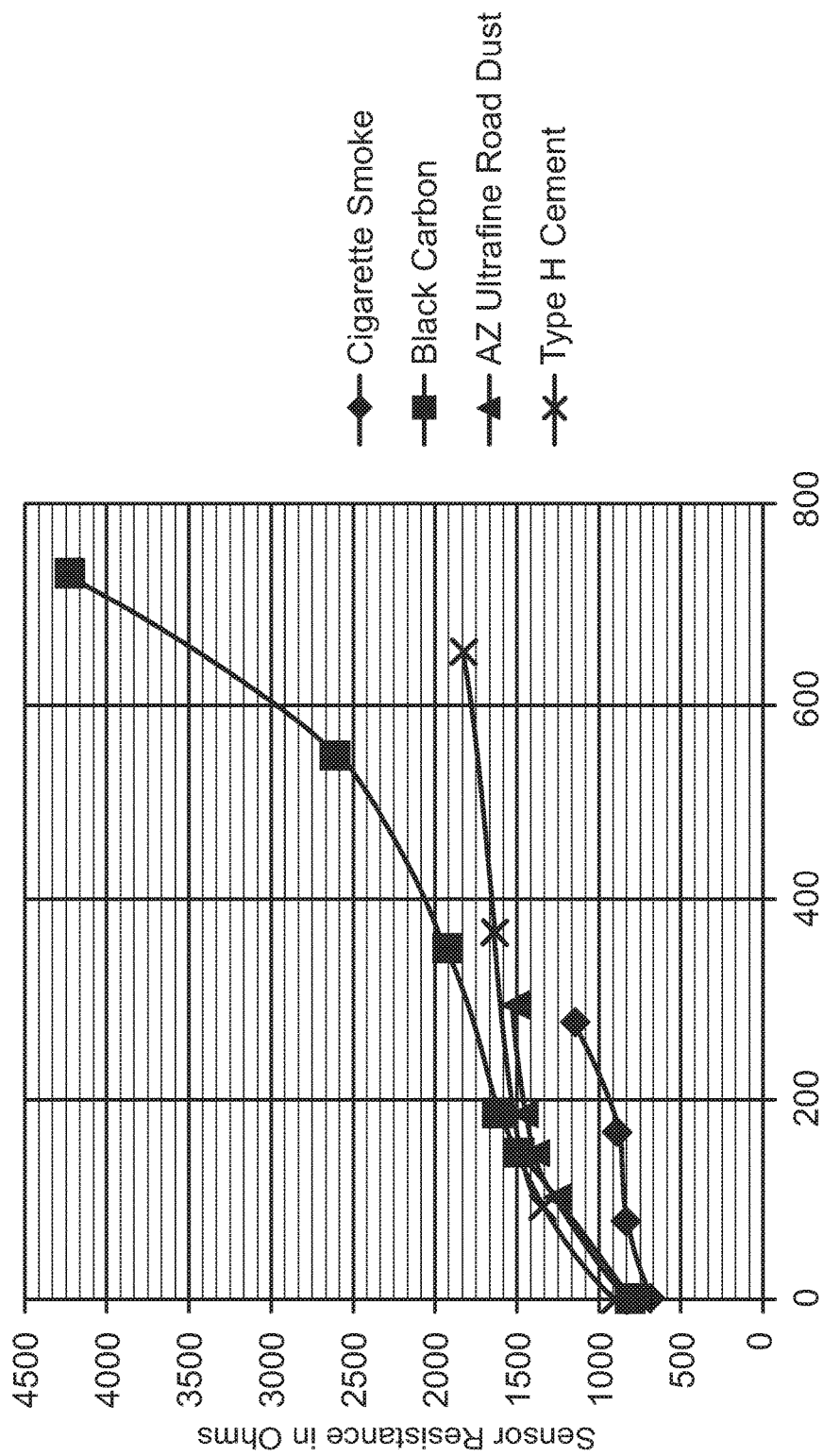
FIG. 5 shows a calibration graph of known materials with a system in accordance with embodiments of the present disclosure.
Figure 6:
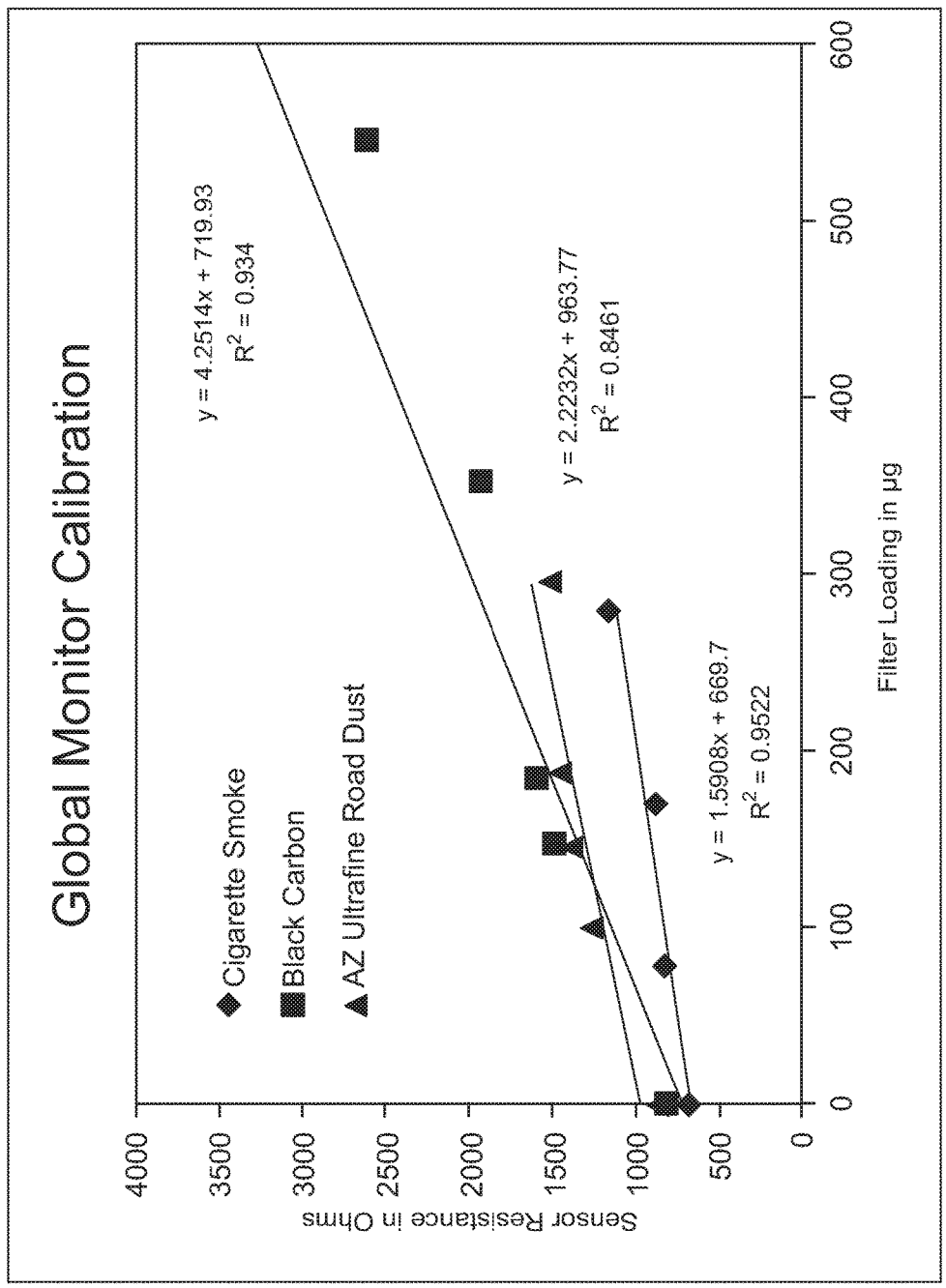
FIG. 6 shows plots of linear fits of data from FIG. 5.

In an experiment, calibration of the system was performed using some of the aerosols and dusts that are considered industry standards for the American Society of Heating, Refrigerating and Air-Conditioning Engineers, Inc. (ASHRAE) filter testing. Using an aerosol deposition chamber, known amounts of Arizona Fine Road Dust 1573, Class H Cement, and Carbon Black were deposited onto nylon nanofiber filters at different durations to give different loading amounts. The filters were weighed pre- and post-deposition. Four different systems were used to test clean and pre-load filters. For real world testing, multiple systems were installed at a known cigarette smoking location to load filters for different time durations. These smoke loaded filters were both weighed and read by the systems. The results for the standard dusts and cigarette smoke are shown in FIGS. 5 and 6. FIG. 5 shows a calibration graph of known materials with the system. FIG. 6 shows plots of linear fits of data from FIG. 5.

In another experiment, systems were deployed to a cigarette smoking location for parallel air sampling and comparison of the monitors during a 24 hour period. The systems were set up side-by-side with the sample inlets directly positioned by the main area where smoking occurred. The systems were powered on at the same time, and were run continuously until the next day when they were powered down at the same time. Nanofiber filters used in the system test were selected based on their similar initial (clean filter) pressure drops. The filters were weighed pre- and post-tested to determine mass gain from collected particulate matter. The systems performed very similarly to each other having a standard deviation of about 16%. These results are summarized in the following table.

TABLE

| Data for Systems | | | |
|---|---|---|---|
| System Number | Filter ID | Initial ΔP (Pa) | Filter wt. gain (μg) |
| 3 | 20130822-acc-01 | 21.9 | 149 |
| 4 | 20130822-acc-02 | 22.4 | 115 |
| 5 | 20130822-acc-03 | 22.2 | 124 |
| 6 | 20130822-acc-10 | 22.7 | 145 |
| 8 | 20130822-acc-12 | 21.9 | 170 |
| 9 | 20130822-acc-15 | 21.9 | 165 |
| 10 | 20130822-acc-18 | 21.7 | 114 |
| | Average | | 140.3 |
| | Median | | 145 |
| | Standard Dev. | | 23.0 |
| | Percent Dev. | | 16.0% |

The above table provides data for systems deployed for 24 hours at a cigarette smoking location. Filter polymer composition was polysulfone with polyethylene oxide additive. Additional parameters include an R1 value of 330 ohms, 8 AA batteries for power, and an initial flow rate of 3.4 L/min (0.12 cfm)

Figure 7:
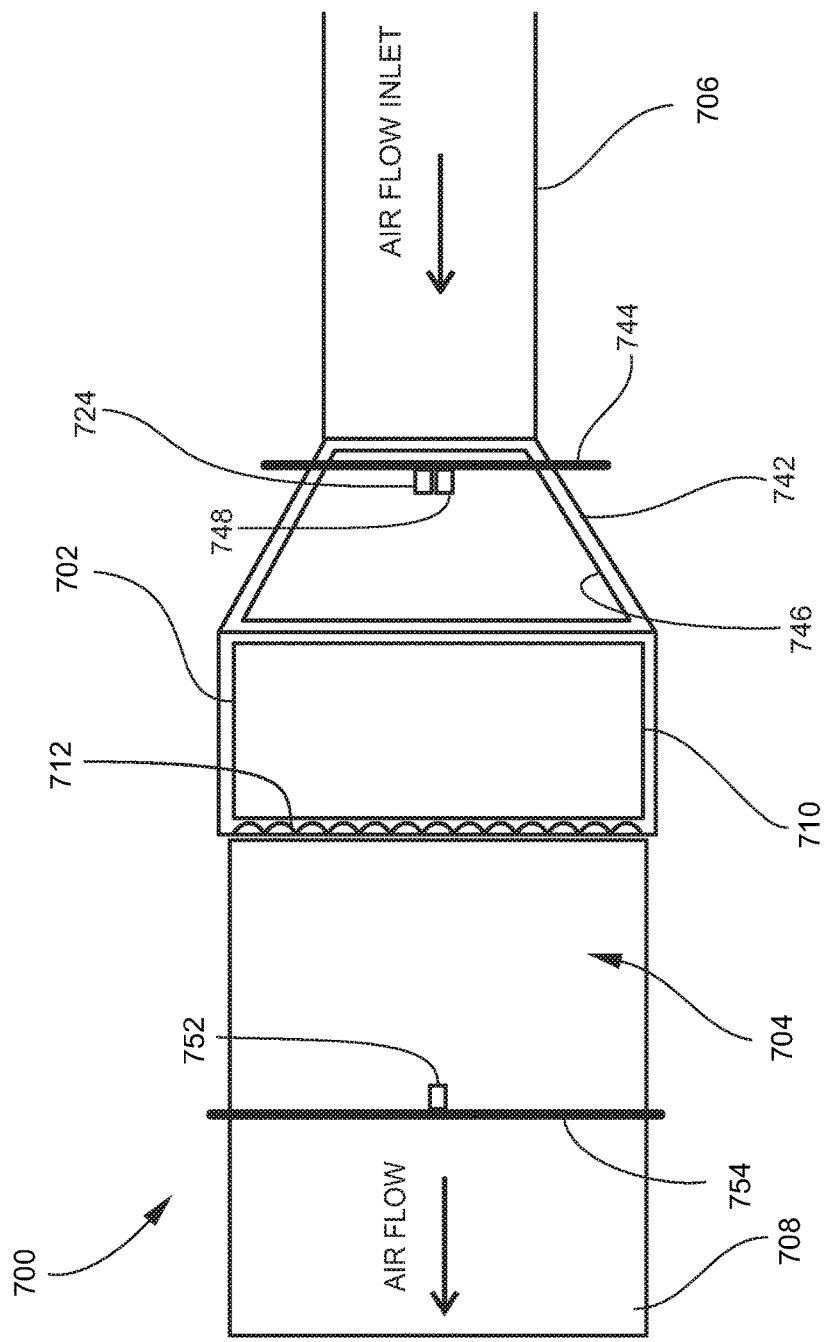
FIG. 7 is a schematic diagram of an example system for particle excitation and capture of subsequent emission in accordance with embodiments of the present disclosure.

In accordance with embodiments, FIG. 7 illustrates a schematic diagram of an example system (or particle detector) 700 for particle excitation and capture of subsequent emission. Referring to FIG. 7, the system 700 includes a housing 702 that defines a sample chamber 704 having a sample or air flow inlet 706 and a sample or air flow outlet 708. The housing 702 is configured to support a particle collection filter 712 in the sample chamber 704, for example by way of a 2-inch filter holder coupling. The sample chamber 704 may include a tapered transition such as a reducing union 742 mounted between the inlet 706 and the particle collection filter 712. The reducing union 742 may be constructed of, for example, black PVC. A light source 724 may be mounted in the sample chamber 704, such as in the reducing union 742 as illustrated. The light source 724 may be or include, for example, a UV LED or other LED (the LED color may depend on the desired excitation). The light source 724 may be mounted on a thin plastic rod 744 of about $\frac{1}{16}^{th}$ inch in diameter so as to not impede or restrict the air inlet flow rate. Interior walls 710 of the reducing union 742 may be covered with a suitable large-area solar cell material 746 (or other type of photo-responsive, e.g., photovoltaic or photoelectric material), which may be flexible so as to conform to the tapered geometry of the reducing union 742. Alternatively, the flexible solar cell material 746 may be conformally wrapped around the outside surface of the reducing union 742. The flexible solar cell material 746 may serve as the light detector for measuring scattered and/or fluorescent emission from the collected particles. In some embodiments, the flexible solar cell material 746 may covered with a uniform transparent filter material configured to block the selected LED emission wavelength(s).

The solar cell material 746 may be composed of any material (or composite of two or more materials) exhibiting efficient photo-responsive (e.g., photovoltaic or photoelectric) activity (e.g., a photovoltaic or photoelectric material) and sufficiently sensitive over the range of wavelengths of measurement light contemplated for the system 700. For example, the photo-responsive material may be a thin-film inorganic, organic, or hybrid organic/inorganic semiconductor, one non-limiting example being amorphous silicon. The photo-responsive material may generally be a material having at least one electrical characteristic (current, voltage, or resistance) that varies in proportion to light incident thereon.

In some embodiments, the photo-responsive material is a photovoltaic (PV) material that produces both a current response and a voltage response to photons incident on its surface. For low light conditions, both a current response and voltage response are observed and are proportional to the amount of photons striking the PV material. The open-circuit voltage (OCV) of a PV material may show a measurable response to low-level particulate concentration changes (e.g., less than 100 #/cm$^3$), due to the logarithmic response relationship between increases in low-level incident light (<<0.1 Suns; or the amount of incident photons corresponding to elastic scattering from particles or fluorescence emissions) and the resulting increase in OCV. In other cases, such as high particle concentrations, measurement of the current response of the PV material may be more useful.

In a typical embodiment, at least one side of the photo-responsive material is supported by a flexible substrate (e.g., a polymer layer or film such as polyimide). In some embodiments the photo-responsive material may be completely encapsulated by (or embedded in) the substrate, or sandwiched between the substrate and an additional encapsulating layer or film, to protect the photo-responsive material from the operating environment. Any layer or film covering the photon collecting side of the photo-responsive material should be optically transparent. In some embodiments, the photon collecting side may be covered by a transparent electrode. In some embodiments, the photon collecting side may be covered by a layer or film of an optical filter material, examples of which are described below.

The photo-responsive material may completely or substantially completely surround the reducing union 742 (or other desired portion of the sample chamber 704) to provide a detection area spanning 360° or nearly 360° around the longitudinal axis of the reducing union 742. The photo-responsive material may contiguously surround the reducing union 742. Alternatively, the photo-responsive material may include a plurality of discrete units or cells of photo-responsive material spaced apart from each other and collectively surrounding the reducing union 742. Such photo-responsive units or cells may be arranged in a one-dimensional (linear) or two-dimensional array. In one non-limiting example, the photo-responsive material may be based on a PV module commercially available from PowerFilm, Inc., Ames, Iowa, USA (e.g., model MP3-37).

As described above, in some embodiments the solar cell material 746 further includes one or more optical filters positioned optically between the photon collecting side of the photo-responsive material and the interior of the reducing union 742 (or other portion of the sample chamber 704 surrounded by the solar cell material 746). That is, the optical filter is positioned such that any measurement light directed toward the photo-responsive material must first pass through the optical filter. In some embodiments, the optical filter is disposed on the photo-responsive material, i.e., directly on the photo-responsive material or on a layer or film covering or encapsulating the photo-responsive material. The optical filter generally may be configured to block one or more ranges of wavelengths, and thus may be a low-pass, high-pass, or band-pass filter. The optical filter may be a composite of two or more optical filters to obtain the desired pass/block characteristics. The optical filter may be a solid (e.g. glass or polymer) or gel (e.g. polymer) material, and may be thin and/or pliable enough to be flexible so as to conformally cover the photo-responsive material. In one non-limiting example, a gel filter may be one commercially available from Rosco Laboratories, Inc., Stamford, Conn., USA. The optical filter may generally be configured for blocking any selected wavelength or range(s) of wavelengths (undesired photons), depending on the application. For example, when measuring autofluorescence, the optical filter may be configured for passing the wavelengths of the fluorescent measurement light while blocking the wavelength of the irradiating light utilized to excite the fluorophores. As another example, when measuring scattering, the optical filter may be configured for passing the wavelength of the irradiating light (and thus the wavelength of the scattered measurement light) while blocking other wavelengths such as, for example, stray ambient light.

When the light source 724 is turned on, material or particulates collected on the particle collection filter 712 may be excited and the light emitted from the material or particulates may be collected by the flexible solar cell material 746. The voltage generated by the flexible solar cell material 746 may be displayed on a volt meter. Another light detector 748, such as photodiode or photoresistor, may also be installed at an upstream location such as the rod 744 to increase detection capabilities. In various embodiments, the system 700 may be suitably modified by changing the LEDs or filters, or solar cell material and diode arrangement.

In some embodiments, an additional light source 752 may be mounted downstream from the particle collection filter 712, such as on a thin rod 754. The additional light source 752 may be utilized in conjunction with the additional light detector 748 for flow control/particle loading sensing. For example, the additional light source 752 may direct light to the particle collection filter 712, and the additional light detector 748 may measure the transmittance of the light through the particle collection filter 712. The output from the additional light detector 748 may utilized by a suitable controller and associated circuitry to regulate a fluid moving device (e.g., fan, not shown) and thereby regulate fluid flow to compensate for particle loading of the particle collection filter 712, as generally described above. The light source 724 utilized to irradiate the particles for measurement and the additional light source 752 utilized for load sensing may generate light at different wavelengths so that the functions of data acquisition and load sensing do not affect each other. For example, the light source 724 may be a UV LED while the additional light source 752 may be a green LED (with the additional light detector 748 being sensitive to the green wavelength).

In experimentation of the system shown in FIG. 7, a UV-LED system was tested. Particularly, two wavelengths (365 nm and 375 nm) were tested. The 375 nm LEDs appeared to provide the best results and are lower cost. Both wavelengths provided detection of TINOPAL® (a fluorescent compound) and *Bacillus atrophaeus* added to the test filters. The sensor response was demonstrated to be fairly linear allowing for differing amounts of the two test species being detected.

The present disclosure further encompasses various other embodiments providing various combinations of one or more features of the embodiments described above and illustrated in FIGS. 1 to 7. Moreover, other embodiments may include one or more features disclosed in U.S. Provisional Patent Application Ser. No. 62/039,512, filed Aug. 20, 2014, titled "DEVICES, SYSTEMS AND METHODS FOR DETECTING PARTICLES," the content of which is incorporated by reference herein in its entirety.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A sample monitoring control system comprising:
    a housing comprising a sample inlet and sample outlet, and enclosing a sample chamber;

a particle collection filter positioned in the sample chamber and configured to collect particles of a sample for analysis;

a fluid moving device for moving the sample through the particle collection filter;

a light source configured to direct irradiating light towards the particle collection filter;

a light detector comprising a photo-responsive material configured to receive measurement light emitted from particles of the sample, wherein the photo-responsive material is flexible and conformally disposed on an inside surface or an outside surface of the housing;

another light detector positioned to receive the irradiating light passing through the particle collection filter and configured to generate a signal representative of an amount of the received light; and a controller configured to receive the signal and to control the fluid moving device based on the amount of the received light, wherein the control of the fluid moving device comprises a control selected from the group consisting of:

the controller is configured to control the fluid moving device to increase an output of the fluid moving device in response to a decrease in the amount of the received light;

the controller is configured to control the fluid moving device to decrease an output of the fluid moving device in response to an increase in the amount of the received light; and both of the foregoing.

2. The sample monitoring control system of claim 1, wherein the particle collection filter comprises a nanofiber filter.

3. The sample monitoring control system of claim 1, wherein the particle collection filter comprises a plurality of fibers.

4. The sample monitoring control system of claim 3, wherein the fibers are formed into a fiber mat and configured to collect particles thereon.

5. The sample monitoring control system of claim 3, wherein the fibers have an average fiber diameter of less than 500 nanometers.

6. The sample monitoring control system of claim 1, wherein the fluid moving device and the another light detector are positioned within the sample chamber, and wherein the particle collection filter is positioned between the light detector and the light source.

7. The sample monitoring control system of claim 1, wherein the light source is configured to emit the irradiating light in a wavelength range effective for inducing autofluorescence in one or more types of bioparticles.

8. The sample monitoring control system of claim 1, wherein the light source comprises a light emitting diode (LED).

9. The sample monitoring control system of claim 1, wherein the controller has a configuration selected from the group consisting of:

the controller comprises a plurality of resistors and a voltage regulator; and the controller comprises a microcontroller.

10. The sample monitoring control system of claim 1, further comprising a data acquisition device configured to measure a response of the photo-responsive material selected from the group consisting of: a voltage response; a current response; a resistance response; or a combination of two or more of the foregoing.

11. The sample monitoring control system of claim 1, wherein the particle collection filter has a configuration selected from the group consisting of:

the particle collection filter has a transmittance of at least 30%;

the particle collection filter has a transmittance of at least 50%;

the particle collection filter has a filtration efficiency of at least 85%;

the particle collection filter has a filtration efficiency of greater than 90%;

the particle collection filter is configured to provide a pressure drop not more than 600 Pa; and the particle collection filter is configured to provide a pressure drop not more than 150 Pa.

12. The sample monitoring control system of claim 1, wherein the controller is configured to control the fluid moving device based on the amount of the irradiating light received by the another light detector to maintain movement of the sample at a constant or near constant flow rate.

* * * * *